United States Patent
Akui (10) Patent No.: US 11,992,189 B2
(45) Date of Patent: May 28, 2024

(54) ENDOSCOPE

(71) Applicant: OLYMPUS CORPORATION, Tokyo (JP)

(72) Inventor: Nobuaki Akui, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 731 days.

(21) Appl. No.: 17/124,866

(22) Filed: Dec. 17, 2020

(65) Prior Publication Data

US 2021/0127951 A1 May 6, 2021

Related U.S. Application Data (63) Continuation of application No. PCT/JP2018/025396, filed on Jul. 4, 2018.

(51) Int. Cl.
*A61B 1/005* (2006.01)

(52) U.S. Cl.
CPC .......... *A61B 1/0057* (2013.01); *A61B 1/0055* (2013.01)

(58) Field of Classification Search
CPC ............................. A61B 1/0055; A61B 1/0057
See application file for complete search history.

(56) References Cited

U.S. PATENT DOCUMENTS

| | | | |
|---|---|---|---|
| 2009/0062606 A1* | 3/2009 | Ueda ................ | A61B 1/00078 600/114 |
| 2010/0280525 A1* | 11/2010 | Alvarez ............ | A61B 1/0055 606/130 |
| 2012/0071864 A1 | 3/2012 | Banju et al. | |
| 2013/0150673 A1* | 6/2013 | Kakehashi ......... | A61B 1/0676 600/142 |
| 2013/0197306 A1* | 8/2013 | Armand ............ | A61B 1/0055 600/109 |
| 2014/0066716 A1 | 3/2014 | Arai et al. | |

(Continued)

FOREIGN PATENT DOCUMENTS

| EP | 2505117 A1 | 10/2012 |
|---|---|---|
| EP | 2712538 A1 | 4/2014 |

(Continued)

OTHER PUBLICATIONS

International Search Report dated Sep. 18, 2018 issued in PCT/JP2018/025396.

*Primary Examiner* — Aaron B Fairchild
(74) *Attorney, Agent, or Firm* — Scully, Scott, Murphy & Presser, P.C.

(57) ABSTRACT

An endoscope includes: a first bending wire that is connected with a first connection part of a bending portion of an insertion portion inserted into a subject and bends the entire bending portion in a first bending direction by pulling; a second bending wire that is connected with a second connection part of the bending portion positioned on a proximal end side of the first connection part and bends a proximal end side part of the bending portion on the proximal end side of the second connection part in the first bending direction by pulling; an operation lever that pulls the first bending wire to the proximal end side; an operation lever that pulls the second bending wire to the proximal end side; and a coil pipe into which the first and second bending wires are inserted at a position on the proximal end side of the bending portion.

18 Claims, 7 Drawing Sheets

(56) References Cited

U.S. PATENT DOCUMENTS

| | | |
|---|---|---|
| 2015/0133959 A1 | 5/2015 | Kato |
| 2016/0100746 A1 | 4/2016 | Okazaki et al. |
| 2017/0042412 A1* | 2/2017 | Takemoto ............ A61B 1/0057 |
| 2017/0095138 A1 | 4/2017 | Nakade et al. |
| 2018/0242820 A1* | 8/2018 | Tanaka ................. A61B 1/0051 |

FOREIGN PATENT DOCUMENTS

| | | |
|---|---|---|
| EP | 3011889 A1 | 4/2016 |
| EP | 3138465 A1 | 3/2017 |
| JE | 2013-248116 A | 12/2013 |
| JP | 2007-289389 A | 11/2007 |
| JP | 2011-200428 A | 10/2011 |
| JP | 2013-202304 A | 10/2013 |
| JP | 2015-2843 A | 1/2015 |
| WO | WO 2011/111258 A1 | 9/2011 |
| WO | WO 2012/040442 A1 | 3/2012 |
| WO | WO 2013/150871 A1 | 10/2013 |
| WO | WO 2014/203432 A1 | 12/2014 |
| WO | WO 2016/052145 A1 | 4/2016 |

\* cited by examiner

ENDOSCOPE

CROSS REFERENCE TO RELATED APPLICATION

This application is a continuation application of PCT/JP2018/025396 filed on Jul. 4, 2018, the entire contents of which are incorporated herein by this reference.

BACKGROUND OF THE INVENTION

1. Field of the Invention

The present invention relates to an endoscope including a bending portion at an insertion portion.

2. Description of the Related Art

Endoscopes have been widely used in medical and industrial fields. An endoscope includes an elongated insertion portion, and an observation window is provided at a distal end portion of the insertion portion. A user of the endoscope, such as a surgeon, can perform examination, treatment, or the like with the endoscope by causing a display device to display an endoscope image based on an object image incident through the observation window.

The bending portion is provided at the proximal end of the distal end portion of the insertion portion, and the user of the endoscope can bend the bending portion in a predetermined direction by operating a bending operation member provided on an operation portion of the endoscope. Thus, while viewing the endoscope image, the user can press the insertion portion and bend the bending portion to move the distal end portion of the insertion portion closer to a desired site in a subject.

In some endoscopes, a treatment instrument insertion channel is provided in the insertion portion. For example, Japanese Patent Application Laid-Open Publication No. 2011-200428 discloses an endoscope in which the bending portion is bendable in two directions and the treatment instrument insertion channel is provided in the insertion portion. The user can insert a treatment instrument into the treatment instrument insertion channel, protrude a distal end portion of the treatment instrument through a treatment instrument opening of the distal end portion of the insertion portion, and perform treatment with the treatment instrument.

SUMMARY OF THE INVENTION

An endoscope according to an aspect of the present invention includes: a bending portion provided in an insertion portion inserted into a subject; a first wire that is connected with a first connection part of the bending portion and bends the entire bending portion in a first bending direction by pulling; a second wire that is connected with a second connection part of the bending portion positioned on a proximal end side of the first connection part and bends a proximal end side part of the bending portion on the proximal end side of the second connection part in the first bending direction by pulling; a first operation member that is connected with the first wire and pulls the first wire to the proximal end side; a second operation member that is connected with the second wire and pulls the second wire to the proximal end side; and a first guide member into which the first wire and the second wire are inserted at a position on the proximal end side of the bending portion.

DETAILED DESCRIPTION OF THE PREFERRED EMBODIMENT

The present invention will be described below with reference to an embodiment.

Note that in each drawing used in the following description, a different scale is applied to each component so that the component has a size recognizable in the drawing, and the present invention is not limited to the number of components, the shape of each component, the ratio of sizes of the components, and the relative positional relation among the components illustrated in the drawings.

Figure 1:
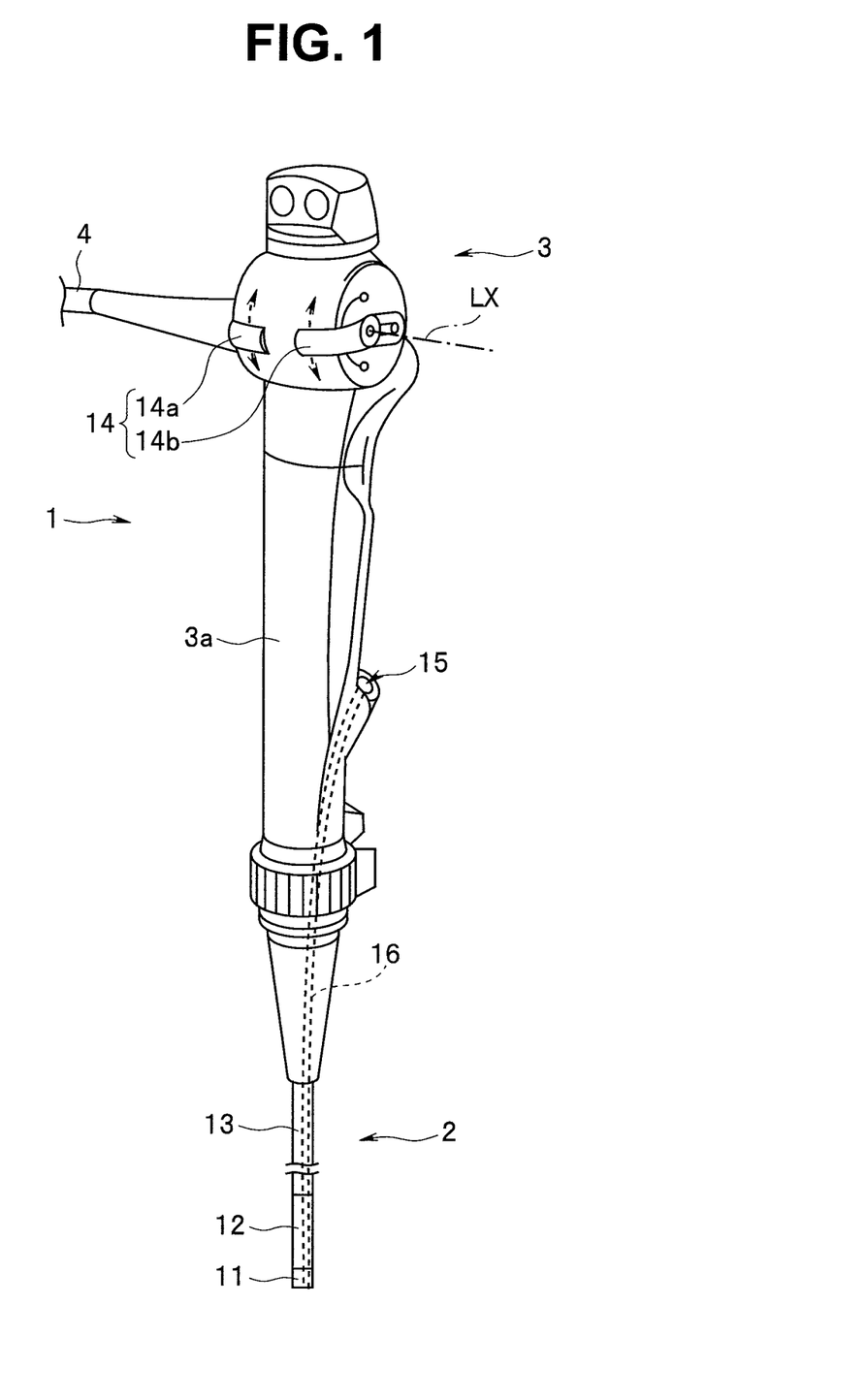
FIG. 1 is a configuration diagram of an endoscope according to an embodiment of the present invention.
Figure 2:
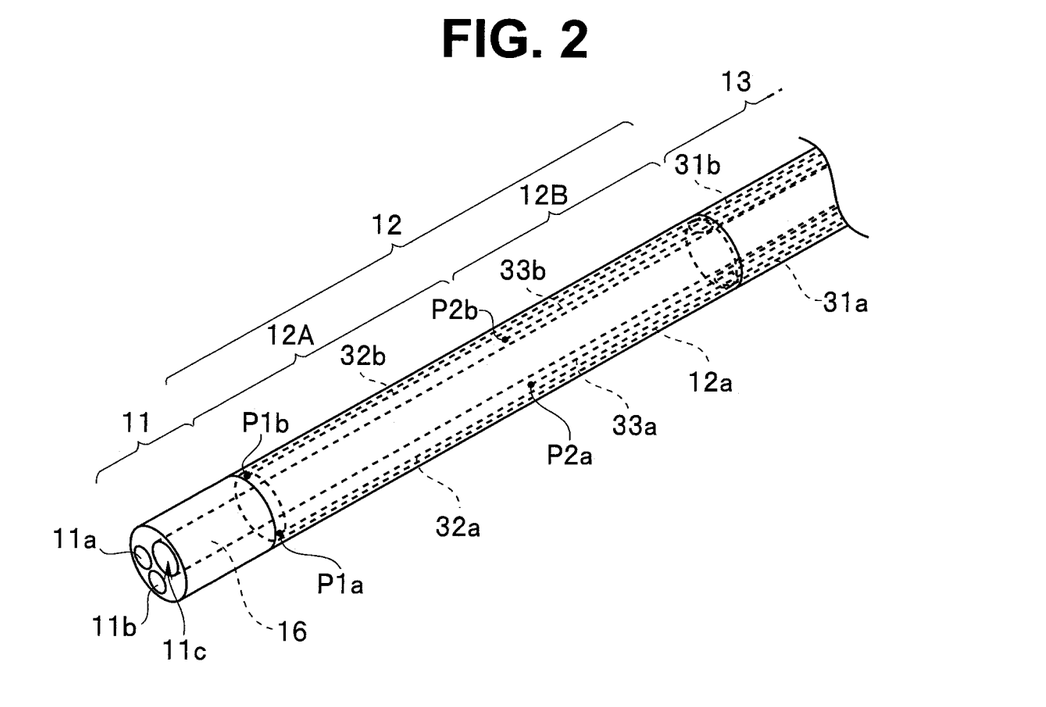
FIG. 2 is a perspective view of a distal end portion and a bending portion of an insertion portion according to the embodiment of the present invention.

FIG. 1 is a configuration diagram of an endoscope according to the embodiment of the present invention. FIG. 2 is a perspective view of a distal end portion and a bending portion of an insertion portion according to the embodiment of the present invention.

An endoscope 1 includes an elongated insertion portion 2, an operation portion 3 connected with the proximal end of the insertion portion 2, and a cable 4 extending from the operation portion 3. A connector (not illustrated) for connection with a main device such as a video processor is provided at the distal end of the cable 4.

The insertion portion 2 includes, sequentially from the distal end, a distal end portion 11, a bending portion 12, and a flexible tube portion 13. The insertion portion 2 is inserted into a subject. In other words, the bending portion 12 is provided in the insertion portion 2 that is inserted into the subject.

The distal end portion 11 includes, on a distal end surface, an observation window 11a, an illumination window 11b, and a treatment instrument opening 11c as illustrated in FIG. 2. An object is irradiated with illumination light emitted from the illumination window 11b. Reflected light of the illumination light from the object is incident on the observation window 11a.

An image pickup unit is provided behind the observation window 11a. A distal end surface of a light guide of an optical fiber bundle is disposed behind the illumination window 11b. The image pickup unit photoelectrically converts an object image and outputs an image pickup signal. The image pickup signal is supplied to the video processor, and the video processor generates an endoscope image and outputs an image signal to a display device.

Thus, a user of the endoscope 1 can perform examination or treatment in the subject while viewing the endoscope image displayed on the display device.

The bending portion 12 includes a bending mechanism. A bending pipe 12a is disposed in the bending portion 12. The configuration of the bending portion 12 will be described later.

The flexible tube portion 13 has a configuration in which a flex, a braid, and an external skin resin are stacked from the inner side. The flex is a helical pipe as a flexible member having a shape in which a flat plate material is wound in a helical shape. The braid is a metal net pipe. The external skin resin is formed at an outer peripheral part of the braid and partially included between metal strands of the braid. Accordingly, the flexible tube portion 13 has stiffness and flexibility to some extent.

An operation lever portion 14 is provided as a bending operation member to the operation portion 3. The operation lever portion 14 includes two operation levers 14a and 14b. The operation levers 14a and 14b are rotatable about a predetermined axis LX of the operation portion 3 as illustrated with dotted-line arrows. The user can bend the bending portion 12 by operating the operation lever portion 14.

Note that in the present embodiment, the bending operation member of the operation portion 3 includes the two operation levers 14a and 14b, but may include two bending knobs of a circular plate shape in place of the two operation levers 14a and 14b. In this case, the two bending knobs are configured to be coaxially and independently rotatable.

A treatment instrument insertion port 15 is provided in the operation portion 3. A treatment instrument insertion channel into which a treatment instrument can be inserted is formed in the insertion portion 2. The treatment instrument insertion port 15 is an opening at the proximal end of a treatment instrument insertion channel 16, and the treatment instrument opening of the distal end portion 11 is an opening at the distal end of the treatment instrument insertion channel 16.

The treatment instrument insertion channel also functions as a reflux path through which liquid such as normal saline is fed into the subject and the liquid returns from inside the subject.

The user can bend the bending portion 12 in a predetermined direction by operating the operation lever portion 14 of the operation portion 3. For example, the user operates the operation lever portion 14 with fingers of the left hand while grasping the insertion portion 2 with the right hand and grasping a grasping portion 3a of the operation portion 3 with the left hand.

The user can view the endoscope image and bend the bending portion 12 to move the distal end portion 11 of the insertion portion 2 further into a tract in the subject.

Figure 3:
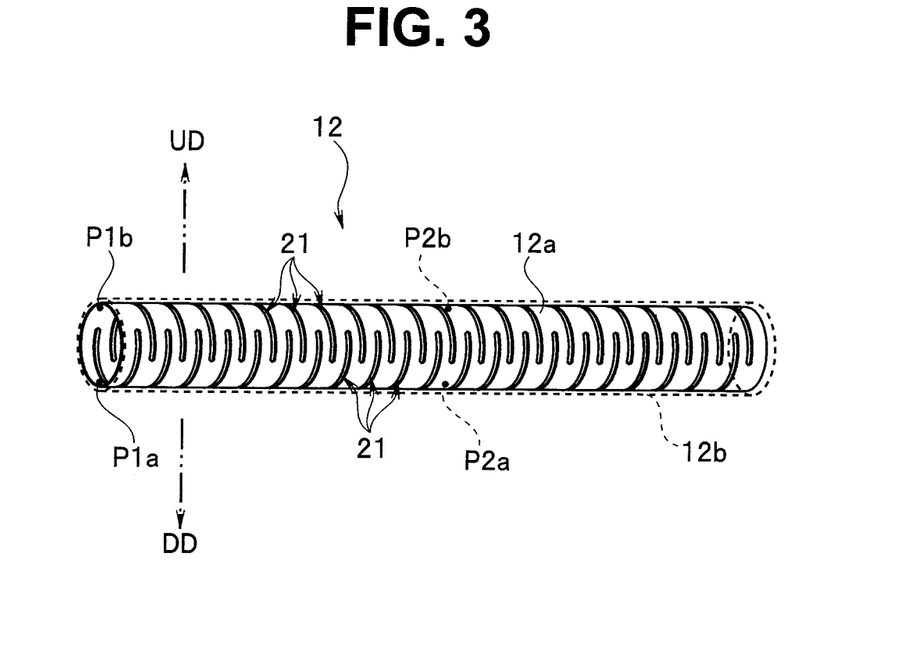
FIG. 3 is a perspective view of a bending pipe disposed in the bending portion according to the embodiment of the present invention.
Figure 4:
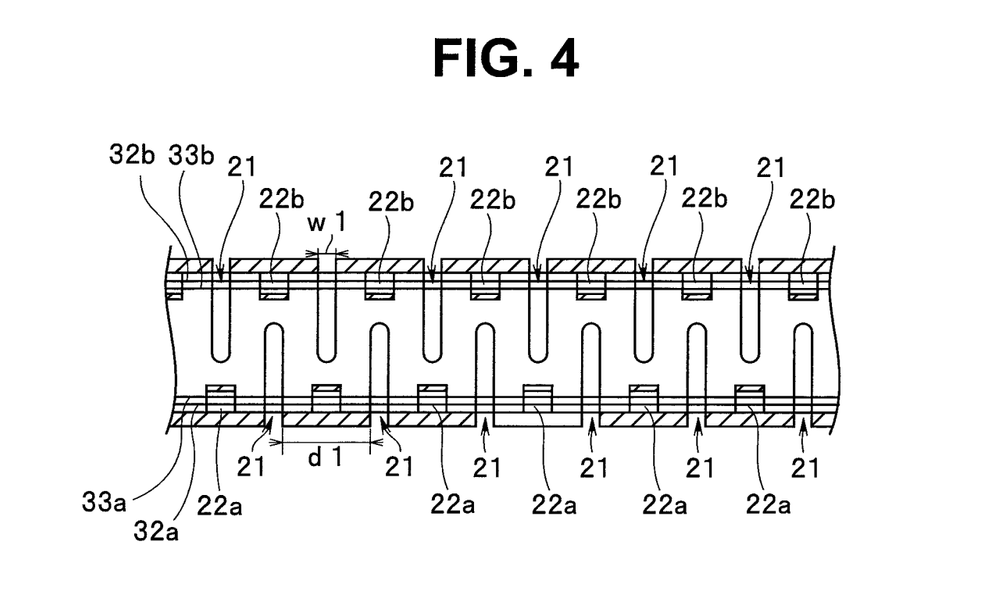
FIG. 4 is a partial cross-sectional view of the bending portion according to the embodiment of the present invention.

The following describes the configuration of the bending portion 12 with reference to FIGS. 2, 3, and 4.

FIG. 3 is a perspective view of the bending pipe 12a disposed in the bending portion 12. FIG. 4 is a partial cross-sectional view of the bending portion 12.

The bending portion 12 includes the bending pipe 12a. As illustrated in FIG. 3, the bending portion 12 includes the bending pipe 12a and an external skin 12b illustrated with dotted lines. The bending pipe 12a is mainly configured as a cylindrical pipe member formed of superelastic alloy. Examples of superelastic alloy materials configuring the bending pipe 12a include Ni—Ti (nickel titanium), titanium alloy, beta titanium, pure titanium, 64 titanium, A7075, and aluminum alloy.

A plurality of bending slits 21 each having a partially arc shape, penetrating from the outer peripheral surface side to the inner peripheral surface side of the bending pipe 12a, and extending in the circumferential direction of the bending pipe 12a are provided in the bending pipe 12a at a predetermined interval in a longitudinal axial direction by, for example, laser fabrication.

Each bending slit 21 has a width w1 in the longitudinal axial direction of the bending pipe 12a. The plurality of bending slits 21 are formed in a staggered manner at positions on one side and the other side in a direction orthogonal to the longitudinal axial direction of the bending pipe 12a.

Specifically, in the bending pipe 12a, a plurality of bending slits 21 opened in the same direction are arrayed in line at an interval dl in the longitudinal axial direction of the bending pipe 12a on one side of the bending pipe 12a, which corresponds to an upper side in a bending direction of the bending portion 12.

In addition, in the bending pipe 12a, a plurality of bending slits 21 opened in the same direction are arrayed in line at the interval dl in a longitudinal axial direction of the bending pipe 12a on the other side of the bending pipe 12a, which corresponds to a lower side in the bending direction of the bending portion 12.

The bending slits 21 arrayed on one side of the bending pipe 12a are disposed at positions staggered with respect to the bending slits 21 arrayed on the other side of the bending pipe 12a.

Thus, the bending pipe 12a can be bent in a first direction UD on the upper side of the bending portion 12 and in a second direction DD on the lower side of the bending portion 12 in FIG. 3.

As illustrated in FIG. 2, in the flexible tube portion 13 of the insertion portion 2, two coil pipes 31a and 31b made of stainless steel are disposed symmetrically with respect to a central axis CO of the insertion portion 2. Two bending wires 32a and 33a made of stainless steel are inserted into the coil pipe 31a. Two bending wires 32b and 33b made of stainless steel are inserted into the coil pipe 31b. A distal end part of each of the coil pipes 31a and 31b is fixed to a distal end part of the flexible tube portion 13 by welding or the like.

The bending wires 32a and 32b are one wire, and a central part of the wire is hung on a pulley in the operation portion 3. The bending wires 33a and 33b are one wire, and a central part of the wire is hung on a pulley different from the pulley on which the bending wires 32a and 32b are hung in the operation portion 3.

One of the pulleys is connected with the operation lever 14a and rotates in accordance with motion of the operation lever 14a. The other pulley is connected with the operation lever 14b and rotates in accordance with motion of the operation lever 14b.

Thus, as the operation lever 14a rotates about the axis LX of the operation portion 3, one of the bending wires 32a and 32b is pulled to the proximal end side. As the operation lever 14b rotates about the axis LX of the operation portion 3, one of the bending wires 33a and 33b is pulled to the proximal end side.

As the user moves the operation lever 14a about the axis LX, the bending wires 32a and 32b move in the insertion portion 2 so that one of the two bending wires 32a and 32b is pulled and the other is relaxed.

Similarly, the operation lever 14b is rotatable about the axis LX of the operation portion 3. Thus, as the user moves the operation lever 14b about the axis LX, the bending wires 33a and 33b move in the insertion portion 2 so that one of the two bending wires 33a and 33b is pulled and the other is relaxed.

As illustrated in FIG. 4, a plurality of wire guides 22a for the bending wires 32a and 33a are provided on the inner peripheral surface of the bending pipe 12a in parallel to a central axis of the bending pipe 12a by welding or the like. A plurality of wire guides 22b for the bending wires 32b and 33b are provided on the inner peripheral surface of the bending pipe 12a in parallel to the central axis of the bending pipe 12a.

Each of the wire guides 22a and 22b is made of metal such as stainless steel and is, for example, a ring-shaped member.

Note that the wire guides 22a and 22b may be lance bending portions formed at thin-walled parts of the bending pipe 12a by cutting and bending through press fabrication. Specifically, each lance bending portion is formed by cutting two parallel slits and bending a part between the two slits by pressing. This lance bending portion serves as a wire guide.

The bending wires 32a and 33a are inserted into the plurality of wire guides 22a in the bending pipe 12a. The bending wires 32b and 33b are inserted into the plurality of wire guides 22b in the bending pipe 12a.

Figure 5:
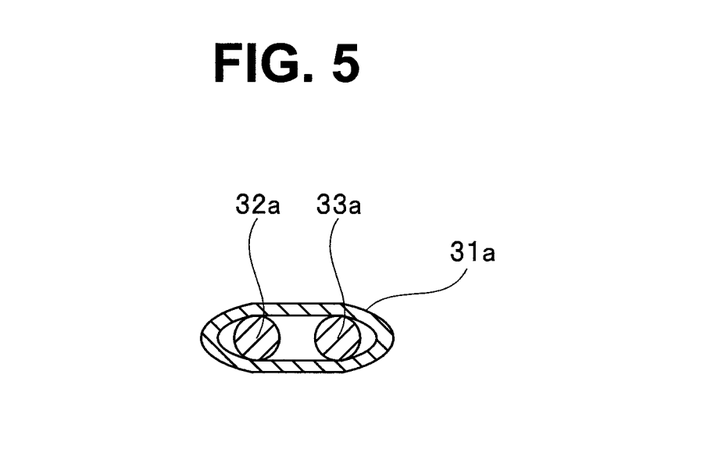
FIG. 5 is a cross-sectional view of a coil pipe into which two bending wires are inserted according to the embodiment of the present invention.

FIG. 5 is a cross-sectional view of the coil pipe 31a into which the two bending wires 32a and 33a are inserted. As illustrated in FIG. 5, the coil pipe 31a has a flat sectional shape when viewed in a direction orthogonal to a longitudinal axial direction of the insertion portion 2. The two bending wires 32a and 33a are inserted into the flat coil pipe 31a, and the coil pipe 31a guides motion of the two bending wires 32a and 33a.

Specifically, the shape of a section of the coil pipe 31a, which is orthogonal to the longitudinal axial direction of the insertion portion 2, is flat, and the coil pipe 31a configures a guide member into which the two bending wires 32a and 33a are inserted at a position on the proximal end side of the bending portion 12.

The distal end of the bending wire 32a protruding from the distal end of the coil pipe 31a is fixed to the inner peripheral surface of a distal end part of the bending pipe 12a by fixation such as welding. In FIGS. 2 and 3, the distal end of the bending wire 32a is fixed to the bending pipe 12a at the position of a point P1a.

The distal end of the bending wire 33a protruding from the distal end of the coil pipe 31a is fixed to the inner peripheral surface of a halfway part of the bending pipe 12a, the inner peripheral surface of a central part in this example, by fixation such as welding. In FIGS. 2 and 3, the distal end of the bending wire 33a is fixed to the bending pipe 12a at the position of a point P2a.

As illustrated in FIG. 2, when a distal end side part 12A is part of the bending portion 12 on the distal end side of the point P2a, and a proximal end side part 12B is part of the bending portion 12 on the proximal end side of the point P2a, the bending wire 32a extends through the distal end side part 12A and the proximal end side part 12B of the bending portion 12, and the bending wire 33a extends only through the proximal end side part 12B of the bending portion 12. In other words, the bending wire 32a is inserted across the entire bending portion 12, but the bending wire 33a is inserted across only the proximal end side part of the bending portion 12.

Note that the coil pipe 31b into which the two bending wires 32b and 33b are inserted has a configuration same as the configuration of the coil pipe 31a. As illustrated in FIGS. 2 and 3, the distal end of the bending wire 32b is fixed to the inner peripheral surface of the bending pipe 12a at the position of a point P1b. The distal end of the bending wire 33b is fixed to the inner peripheral surface of the bending pipe 12a at the position of a point P2b.

When the bending pipe 12a is viewed in a central axis direction of the bending pipe 12a, the point P1a and the point P2a are positioned at a central part of the plurality of lower bending slits 21. When the bending pipe 12a is viewed in the central axis direction of the bending pipe 12a, the point P1b and the point P2b are positioned at a central part of the plurality of upper bending slits 21.

As described above, a plurality of coil pipes, the two coil pipes 31a and 31b in this example, as guide members that guide motion of two bending wires are inserted into the flexible tube portion 13.

Specifically, the bending wire 32b is connected with a connection part at the point P1b provided in the bending portion 12 and bends the entire bending portion 12 in a direction opposite to a bending direction of the bending wire 32a by pulling. Similarly, the bending wire 33b is connected with a connection part at the point P2b provided in the bending portion 12 and bends the proximal end side part 12B of the bending portion 12 in a direction opposite to a bending direction by the bending wire 33a by pulling.

When the bending portion 12 is viewed in a longitudinal axial direction of the bending portion 12, the point P1a and the point P2a are positioned on the lower side of the bending portion 12, and the point P1b and the point P2b are positioned on the upper side of the bending portion 12. Connection parts at the points P1a and P2a are positioned at positions symmetric to connection parts at the points P1b and P2b, respectively, with respect to a longitudinal axis of the bending portion 12.

Figure 6:
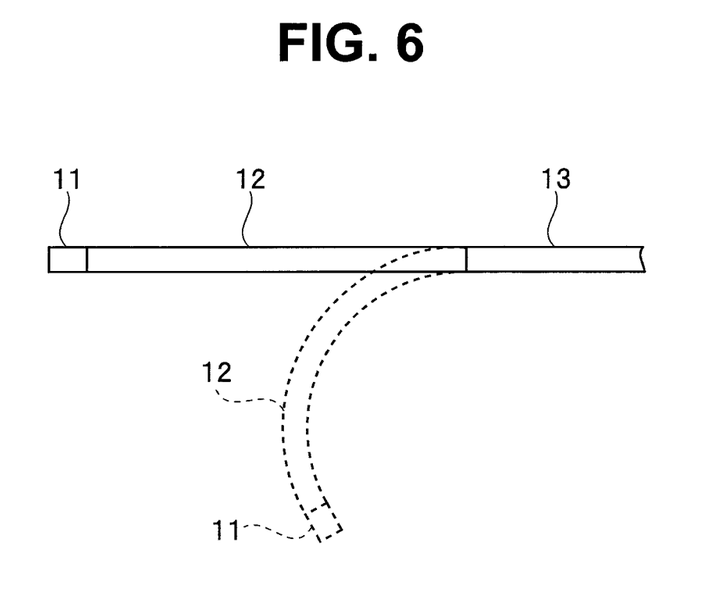
FIG. 6 is a diagram illustrating a bent state of the bending portion according to the embodiment of the present invention.
Figure 7:
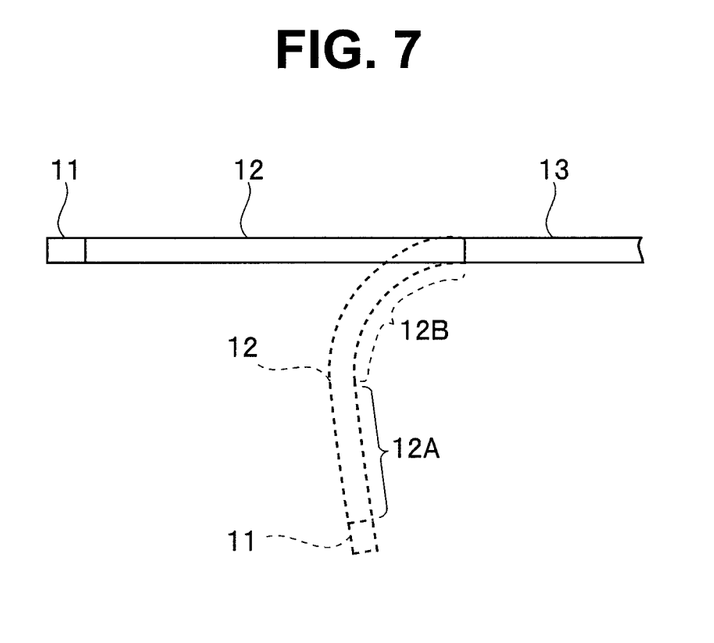
FIG. 7 is a diagram illustrating another bent state of the bending portion according to the embodiment of the present invention.

FIGS. 6 and 7 are each a diagram illustrating a bent state of the bending portion 12. FIG. 6 illustrates the bent state of the bending portion 12 when the bending wire 32a is pulled. Since the distal end of the bending wire 32a is fixed to the distal end of the bending portion 12, the entire bending portion 12 bends to the lower side.

FIG. 7 illustrates the bent state of the bending portion 12 when the bending wire 33a is pulled. Since the distal end of the bending wire 33a is fixed to a central part of the bending portion 12, only the proximal end side part 12B of the bending portion 12 bends to the lower side, but the distal end side part 12A does not bend.

As described above, the bending wires 32a and 32b are connected with the connection parts at the points P1a and P1*b*, respectively, of the bending portion 12 and bend the entire bending portion 12 in the upward or downward bending direction by pulling.

The bending wires 33*a* and 33*b* are connected with the connection parts at the points P2*a* and P2*b*, respectively, of the bending portion 12, the points P2*a* and P2*b* being positioned on the proximal end side of the connection parts at the points P1*a* and P1*b*, and bend the proximal end side part 12B of the bending portion 12 on the proximal end side of the connection parts at the points P2*a* and P2*b* in the upward or downward bending direction by pulling.

Note that the above-described bending portion 12 has a structure including the bending pipe 12*a* in which a plurality of bending slits 21 are formed, but may have a structure in which a plurality of annular bending pieces are continuously provided.

Note that the above-described bending portion 12 may have a configuration including a multi-lumen tube.

Figure 8:
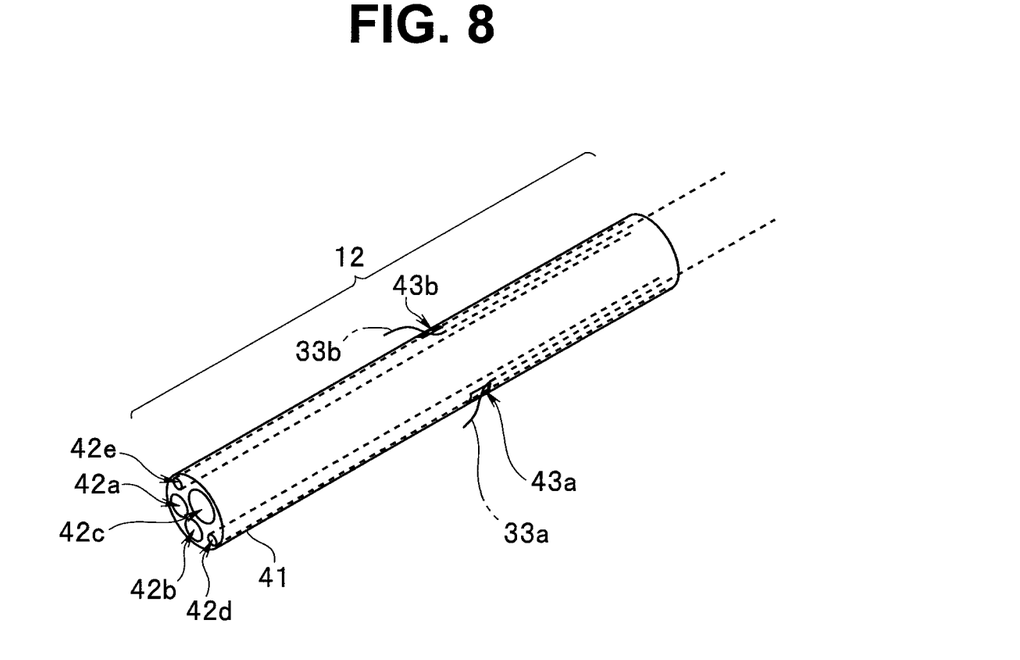
FIG. 8 is a perspective view of a multi-lumen tube provided in the bending portion according to the embodiment of the present invention.

FIG. 8 is a perspective view of a multi-lumen tube provided in the bending portion 12.

As illustrated in FIG. 8, a multi-lumen tube 41 made of soft resin includes a plurality of holes, five holes 42*a*, 42*b*, 42*c*, 42*d*, and 42*e* in this example. The holes 42*a*, 42*b*, and 42*c* correspond to the observation window 11*a*, the illumination window 11*b*, and the treatment instrument opening 11*c*, respectively.

The holes 42*d* and 42*e* are holes for bending wires. The five holes 42*a*, 42*b*, 42*c*, 42*d*, and 42*e* are formed in parallel to one another in a longitudinal axial direction of the multi-lumen tube 41 of a cylinder shape.

The two holes 42*d* and 42*e* are formed close to the outer peripheral surface of the multi-lumen tube 41 at positions symmetric to each other with respect to the central axis of the multi-lumen tube 41 when the insertion portion 2 is viewed from the distal end.

The multi-lumen tube 41 includes an opening 43*a* at a side surface close to the hole 42*d* at a central part of the multi-lumen tube 41 in the longitudinal axial direction. The opening 43*a* communicates with the hole 42*d*. Similarly, the multi-lumen tube 41 includes an opening 43*b* at a side surface close to the hole 42*e* at the central part of the multi-lumen tube 41 in the longitudinal axial direction. The opening 43*b* communicates with the hole 42*e*.

The bending wires 32*a* and 33*a* are inserted into the hole 42*d*, and the bending wires 32*b* and 33*b* are inserted into the hole 42*e*.

Although not illustrated in FIG. 8, the distal end of the bending wire 32*a* is fixed at a distal end portion of the hole 42*d* by a bonding agent or the like. A distal end part of the bending wire 33*a* protrudes out of the multi-lumen tube 41 through the opening 43*a*.

Similarly, although not illustrated in FIG. 8, the distal end of the bending wire 32*b* is fixed at a distal end portion of the hole 42*e* by a bonding agent or the like. A distal end part of the bending wire 33*b* protrudes out of the multi-lumen tube 41 through the opening 43*b*.

Figure 9:
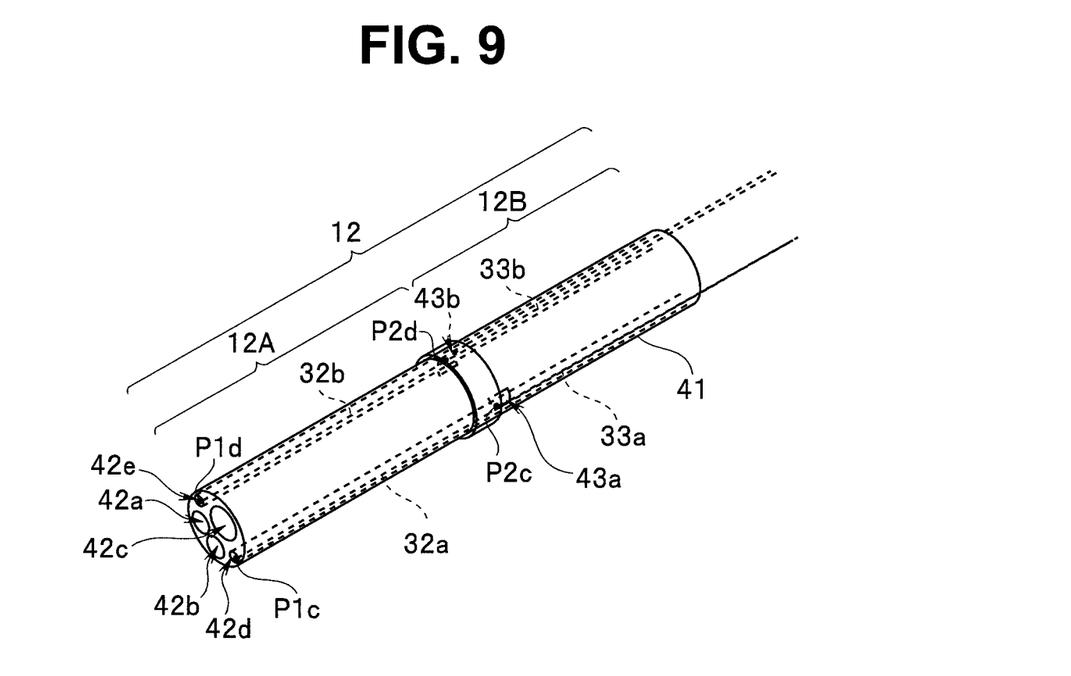
FIG. 9 is a diagram for description of fixation positions and a fixation method of bending wires in the multi-lumen tube according to the embodiment of the present invention.

FIG. 9 is a diagram for description of fixation positions and a fixation method of the bending wires 33*a* and 33*b* in the multi-lumen tube 41.

The multi-lumen tube 41 is inserted from the distal end side of the multi-lumen tube 41 into a ring-shaped member 44 having an inner diameter larger than the outer diameter of the multi-lumen tube 41, and the ring-shaped member 44 is fixed near the two openings 43*a* and 43*b* by a bonding agent or the like.

The distal end part of the bending wire 33*a* protruding out of the opening 43*a* is fixed to a proximal end part of the fixed ring-shaped member 44 by a bonding agent or the like, and the distal end part of the bending wire 33*b* protruding out of the opening 43*b* is fixed as well by a bonding agent or the like.

As a result, the distal end parts of the bending wires 32*a* and 32*b* are each fixed to a distal end part of the multi-lumen tube 41 at points P1*c* and P1*d* by a bonding agent or the like, and the distal end parts of the bending wires 33*a* and 33*b* are fixed by a bonding agent or the like to the ring-shaped member 44 fixed at the center of the multi-lumen tube 41. The two positions of the points P1*c* and P1*d* correspond to the above-described two positions of the points P1*a* and P1*b*.

The distal end of the bending wire 32*a* is fixed at the above-described position of the point P1*a*, and the distal end of the bending wire 32*b* is fixed at the above-described position of the point P1*b*.

Similarly, the distal end of the bending wire 33*a* is fixed at the above-described position of the point P2*a*, and the distal end of the bending wire 33*b* is fixed at the above-described position of the point P2*b*. The two positions of points P2*c* and P2*d* correspond to the two positions of the points P2*a* and P2*b*.

The external skin 12*b* is provided on an outer peripheral part of the multi-lumen tube 41 in FIG. 9.

Thus, the bending portion 12 having the configuration illustrated in FIGS. 8 and 9 can be bent as illustrated in FIGS. 6 and 7 as well.

Specifically, with the configuration illustrated in FIGS. 8 and 9, the entire bending portion 12 bends in the upward or downward bending direction when the bending wire 32*a* or 32*b* is pulled. Only the part 12B on the proximal end side of the points P2*a* and P2*b* bends in the upward or downward direction when the bending wire 33*a* or 33*b* is pulled.

Figure 10:
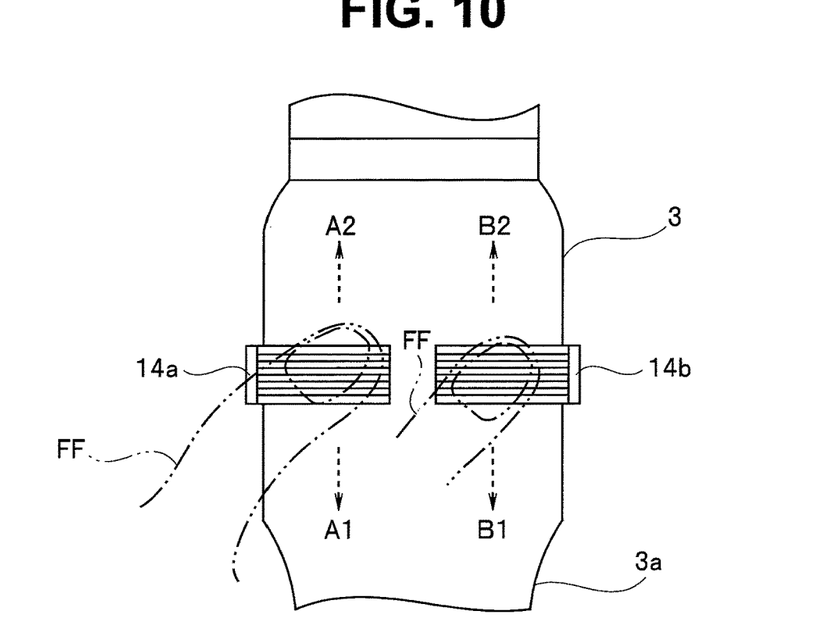
FIG. 10 is a diagram for description of operation of an operation lever of an operation portion according to the embodiment of the present invention.

FIG. 10 is a diagram for description of operation of the operation levers 14*a* and 14*b* of the operation portion 3.

The operation levers 14*a* and 14*b* can be operated by a thumb FF (illustrated with dashed and double-dotted lines) of the left hand when the user grasps the grasping portion 3*a* of the operation portion 3 with, for example, the left hand.

As illustrated in FIG. 10, when the operation lever 14*a* is moved in a dotted-line arrow A1 direction by the thumb FF, the bending wire 32*a* is pulled but the bending wire 32*b* is not pulled. As a result, the bending portion 12 bends as illustrated in FIG. 6.

When the operation lever 14*a* is moved by the thumb FF in the direction of a dotted-line arrow A2 opposite to the direction of the arrow A1, the bending wire 32*b* is pulled but the bending wire 32*a* is not pulled. As a result, the bending portion 12 bends in a direction opposite to the bending direction illustrated in FIG. 6.

In other words, the direction of operation when the bending wire 32*b* is pulled with the operation lever 14*a* is opposite to the direction of operation when the bending wire 32*a* is pulled.

When the operation lever 14*b* is moved in the direction of an arrow B1 by the thumb FF as illustrated in FIG. 10, the bending wire 33*a* is pulled and the bending wire 33*b* is relaxed. As a result, only the proximal end side part 12B of the bending portion 12 bends as illustrated in FIG. 7.

When the operation lever 14*b* is moved in the direction of a dotted-line arrow B2 opposite to the direction of the arrow B1 by the thumb FF, the bending wire 33*b* is pulled but the bending wire 33*a* is not pulled. As a result, only the proximal end side part 12B of the bending portion 12 bends in a direction opposite to the bending direction illustrated in FIG. 7.

Specifically, the direction of operation when the bending wire 33b is pulled with the operation lever 14b is opposite to the direction of operation when the bending wire 33a is pulled.

(Effects)

The following describes bending operation of the bending portion 12 of the endoscope 1 described above.

Figure 11:
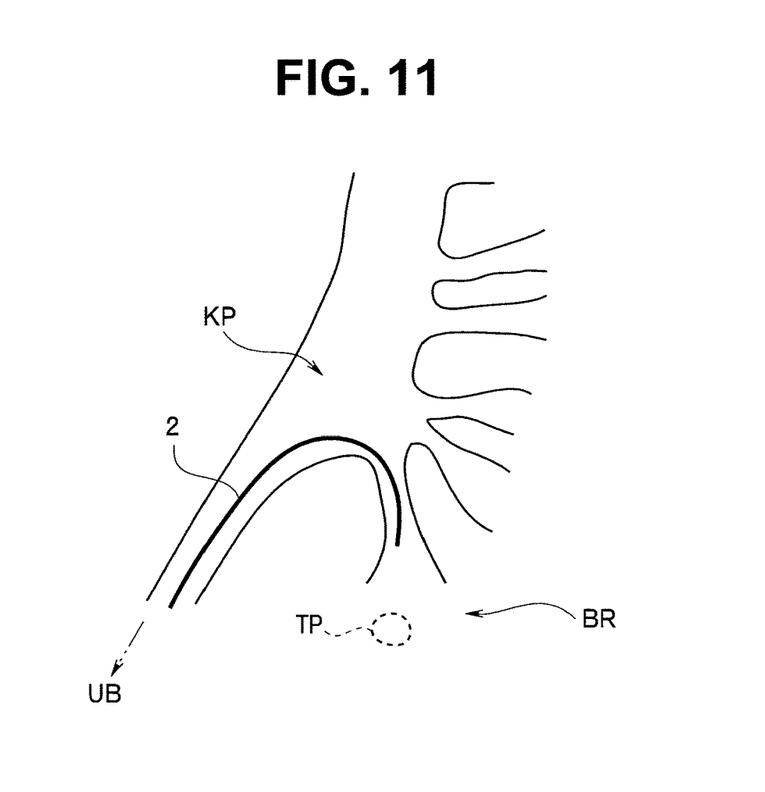
FIG. 11 is a diagram illustrating a state in which the insertion portion of the endoscope according to the embodiment of the present invention is inserted into a subject.

FIG. 11 is a diagram illustrating a state in which the insertion portion 2 of the endoscope 1 is inserted into the subject. In this example, the insertion portion 2 is inserted into the kidney. The kidney includes a plurality of renal calyces. The insertion portion 2 is inserted through the urethra, passes through the bladder UB, and then enters a renal pelvis KP. A surgeon can relatively easily move the distal end portion 11 into each renal calyx other than the lower renal calyx BR.

However, as illustrated in FIG. 11, the bending portion 12 needs to be bent into a folded shape to point the distal end portion 11 of the insertion portion 2 to the lower renal calyx BR close to the bladder UB side. Then, for example, when performing treatment that crushes a kidney stone, the surgeon needs to move the distal end portion 11 closer to a treatment site TP of the kidney stone and perform treatment on the treatment site TP.

When the above-described endoscope 1 is used in such a case, the surgeon pulls the operation lever 14a, for example, in the direction of the arrow A1 to point the insertion portion 2 into the lower renal calyx BR, and accordingly, the entire bending portion 12 bends so that the distal end portion 11 can be inserted into the lower renal calyx BR.

Figure 12:
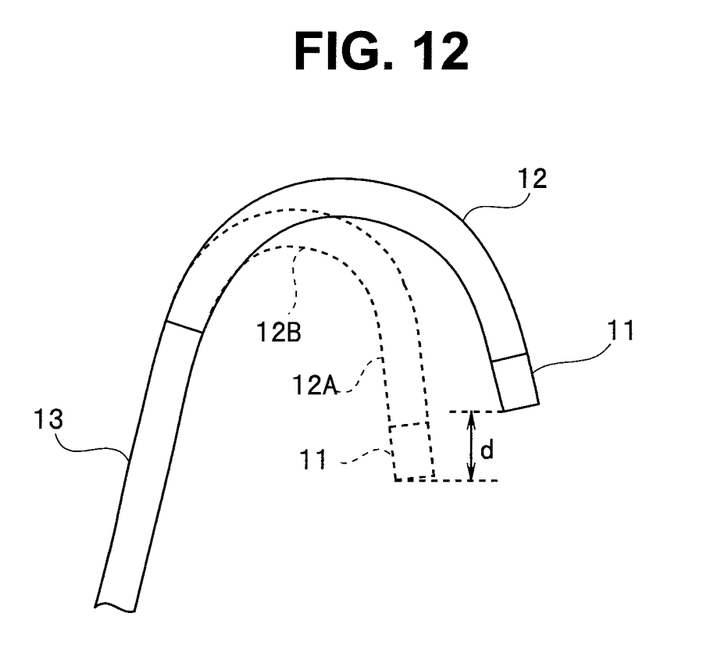
FIG. 12 is a diagram for description of the bent state of the bending portion according to the embodiment of the present invention.

For example, when the bending portion 12 is bent by approximately 150 degrees relative to the direction in which the insertion portion 2 is inserted, the entire bending portion 12 bends as illustrated in FIG. 12. FIG. 12 is a diagram for description of the bent state of the bending portion 12.

The surgeon operates the operation lever 14a while viewing the endoscope image displayed on the display device (not illustrated) so that the entire bending portion 12 largely bends to point the distal end portion 11 to the lower renal calyx BR.

Since the two bending wires 32a and 33a are inserted into the coil pipe 31a, the entire bending portion 12 bends when the operation lever 14a is operated and the bending wire 32a is pulled. Simultaneously, the bending portion 12 bends, and accordingly, the bending wires 32b and 33b are pulled in the distal end direction. In other words, the bending wire 33a simultaneously moves as the bending wire 32a is pulled.

Subsequently, when the surgeon moves the thumb FF to the operation lever 14b and pulls the operation lever 14b in the direction of the arrow B1 while viewing the endoscope image, only the proximal end side part 12B of the bending portion 12 further bends, but the distal end side part 12A of the bending portion 12 is not pulled by the bending wire 32a.

As illustrated with dotted lines in FIG. 12, the proximal end side part 12B of the bending portion 12 further bends from a state illustrated with solid lines. Simultaneously, the thumb FF leaves the operation lever 14a and the bending wire 32a is not pulled any more, and accordingly, the distal end side part 12A of the bending portion 12 returns to a straight shape.

As a result, the distal end portion 11 of the bending portion 12 moves closer to the treatment site TP as illustrated in FIG. 12. The distal end portion 11 can be moved closer to the treatment site TP by a distance d as illustrated in FIG. 12.

While the distal end portion 11 is close to the treatment site TP, the distal end of a laser probe of a laser medical treatment device can be protruded through a treatment instrument opening 12c to crush a kidney stone.

Thus, according to the above-described embodiment, it is possible to provide an endoscope in which the distal end portion 11 of the insertion portion 2 can be moved deep inside a largely bent tract.

In particular, the user can move the distal end portion 11 closer to the treatment site TP through simple operation by moving the distal end portion 11 of the insertion portion 2 deep into a largely bent tract.

Note that the bending portion 12 is bendable in the two directions UD and DD in the above-described embodiment, but may be bendable only in one direction. Specifically, only the bending wires 32a and 33a or only the bending wires 32b and 33b may be inserted into the insertion portion 2.

For example, the operation lever 14a is connected with the bending wire 32a, and the operation lever 14b is connected with the bending wire 33a. As the operation lever 14a is operated to move as the arrow A1, the bending wire 32a is pulled to the proximal end side. Similarly, when the operation lever 14b is operated to move as the arrow B1, the bending wire 33a is pulled to the proximal end side. As a result, for example, the bending portion 12 is bendable only in the downward direction.

The present invention is not limited to the above-described embodiment but may be, for example, changed or modified in various kinds of manners without departing from the gist of the present invention.

What is claimed is:

1. An endoscope comprising:
    a bending portion provided in an insertion portion configured to be inserted into a subject;
    a first wire connected with a first connection part of the bending portion, the first wire configured to bend the entire bending portion in a first bending direction;
    a second wire connected with a second connection part of the bending portion, the second connection part positioned proximally relative to of the first connection part, the second wire configured to bend only a proximal end side part of the bending portion proximal to the second connection part in the first bending direction;
    a first member having a first surface rotatable about a first axis, the first member being operably connected to the first wire to pull the first wire proximally when the first surface is rotated about the first axis;
    a second member having a second surface rotatable about a second axis, the second member being operably connected to the second wire to pull the second wire proximally when the second surface is rotated about the second axis; and
    a first guide tube, separate from the insertion portion, and disposed within the insertion portion, the first wire and the second wire are each inserted into the first guide tube, the first guide tube located at a position proximal to the bending portion.

2. The endoscope according to claim 1, further comprising a plurality of wire guide surfaces configured to guide motion of the first wire and the second wire in the bending portion.

3. The endoscope according to claim 1, wherein the first guide tube has a flat section extending along a longitudinal axial direction of the insertion portion.

4. The endoscope according to claim 1, wherein the bending portion is a bending pipe including a plurality of bending slits.

5. The endoscope according to claim 1, wherein the bending portion is a soft multi-lumen tube including first and second holes formed along the longitudinal axis for holding the first wire and the second wire, respectively.

6. The endoscope according to claim 1, further comprising:
a third wire connected with a third connection part provided in the bending portion, the third wire is configured to bend the entire bending portion in a second bending direction to the first bending direction;
a fourth wire connected with a fourth connection part positioned proximally relative to the third connection part, the fourth wire is configured to bend the proximal end side part in the second bending direction; and
a second guide tube into which the third wire and the fourth wire are inserted at the position proximal to the bending portion, wherein
the first member is connected with the third wire, the first member is configured to pull the third wire proximally, and
the second member is connected with the fourth wire, the second member is configured to pull the fourth wire proximally.

7. The endoscope according to claim 6, wherein the first connection part and the third connection part are positioned at positions symmetric to each other with respect to the longitudinal axis when the bending portion is viewed in a longitudinal axial direction of the bending portion, and the second connection part and the fourth connection part are positioned at positions symmetric to each other with respect to the longitudinal axis when the bending portion is viewed in the longitudinal axial direction of the bending portion.

8. The endoscope according to claim 6, wherein
a direction of operation when the third wire is pulled with the first member is opposite to a direction of operation when the first wire is pulled, and
a direction of operation when the fourth wire is pulled with the second member is opposite to a direction of operation when the second wire is pulled.

9. An endoscope comprising:
an insertion portion including a bending portion, the bending portion including a first connection part and a second connection part, the second connection part positioned proximally relative to the first connection part;
a first wire connected with the first connection part;
a second wire connected with the second connection part;
a first operation lever connected with the first wire;
a second operation lever connected with the second wire;
wherein the first wire is configured to bend the entire bending portion in a first bending direction, and the second wire is configured to bend only a proximal end side part of the bending portion in the first bending direction, the proximal end side part located proximally relative to the second connection part; and
a first guide tube, separate from the insertion portion, and disposed within the insertion portion, the first guide tube receiving each of the first wire and the second wire and located proximally to the bending portion.

10. The endoscope according to claim 9, wherein:
the first operation lever is configured to pull the first wire proximally, and
the second operation lever is configured to pull the second wire proximally.

11. The endoscope according to claim 9, wherein:
the first wire includes a first end and a second end, the second end is located opposite to the first end, the first end of the first wire is fixed to the first connection part, the second end of first wire is fixed to the first operation lever, and
the second wire includes a third end and a fourth end, the fourth end is located opposite to the third end, the third end of second wire is fixed to the second connection part, the fourth end of second wire is fixed to the second operation lever.

12. The endoscope according to claim 9, wherein the first guide tube is configured to guide motion of the first wire and the second wire.

13. The endoscope according to claim 12, further comprising:
a third connection part and a fourth connection part provided on the bending portion, the fourth connection part positioned proximally relative to the third connection part,
a third wire connected with the third connection part;
a fourth wire connected with the fourth connection part; and
a second guide tube receiving the third wire and the fourth wire and located proximally to the bending portion, wherein
the first operation lever is connected with the third wire, and
the second operation lever is connected with the fourth wire.

14. The endoscope according to claim 13, wherein:
the third wire is configured to bend the entire bending portion in a second bending direction opposite to the first bending direction, and
the fourth wire is configured to bend the proximal end side part in the second bending direction.

15. The endoscope according to claim 14, wherein:
the first operation lever is configured to pull the third wire proximally, and
the second operation lever is configured to pull the fourth wire proximally.

16. The endoscope according to claim 13, wherein the first connection part and the third connection part are positioned at positions symmetric to each other with respect to a longitudinal axis, and the second connection part and the fourth connection part are positioned at positions symmetric to each other with respect to the longitudinal axis.

17. The endoscope according to claim 9, wherein the first guide tube has a flat section extending along a longitudinal axial direction of the insertion portion.

18. The endoscope according to claim 9, wherein the bending portion comprises a bending pipe including a plurality of bending slits.

* * * * *